(12) United States Patent
Rapp et al.

(10) Patent No.: US 7,790,771 B1
(45) Date of Patent: Sep. 7, 2010

(54) USE OF TOSYLCHLORAMIDE(S) FOR TREATING DISEASE OF THE SKIN, MUCOUS MEMBRANE, ORGANS AND TISSUES

(75) Inventors: Horst Rapp, Straubenhardt (DE); Friedbert Heck, Bichlerstrasse (DE)

(73) Assignee: Engelhard Arzneimittel GmbH & Co., Niederdorfelden (DE)

( * ) Notice: Subject to any disclaimer, the term of this patent is extended or adjusted under 35 U.S.C. 154(b) by 0 days.

(21) Appl. No.: 10/031,851

(22) PCT Filed: Jul. 21, 2000

(86) PCT No.: PCT/EP00/06997

§ 371 (c)(1),
(2), (4) Date: May 28, 2002

(87) PCT Pub. No.: WO01/07035

PCT Pub. Date: Feb. 1, 2001

(30) Foreign Application Priority Data

Jul. 23, 1999   (DE) ................................ 199 34 585

(51) Int. Cl.
*A01N 33/02* (2006.01)
*A01N 41/10* (2006.01)
*A61K 31/135* (2006.01)
*A61K 31/10* (2006.01)

(52) U.S. Cl. ........................ 514/646; 514/708; 514/709
(58) Field of Classification Search .................. 514/708, 514/709, 646
See application file for complete search history.

(56) References Cited

U.S. PATENT DOCUMENTS 3,317,540 A    5/1967  Wakeman et al.
4,574,084 A *  3/1986  Berger ........................ 424/601

FOREIGN PATENT DOCUMENTS

| DE | 39 13391 A1 | 10/1990 |
|----|---|---|
| DE | 41 37 544 A1 | 5/1993 |
| DE | 41 37 544 C2 | 7/1998 |
| DE | 197 12 565 A1 | 10/1998 |
| EP | 0130690 | 1/1985 |
| FR | 860394 | 1/1941 |
| GB | 1353834 | 5/1974 |
| JP | 47-39515 | 11/1972 |
| JP | 59-222406 | 12/1984 |
| JP | 5-505390 | 8/1993 |
| RU | 2008905 | 3/1994 |
| RU | 2014848 | 6/1994 |
| RU | 2019192 | 9/1994 |
| RU | 2022566 | 11/1994 |
| RU | 2029552 | 2/1995 |
| RU | 2034546 | 5/1995 |
| RU | 2034547 | 5/1995 |
| RU | 2065304 | 8/1996 |
| RU | 2070045 | 12/1996 |
| RU | 2106129 | 3/1998 |
| RU | 2114913 | 7/1998 |
| RU | 2132656 | 7/1999 |
| RU | 2165772 | 4/2001 |
| WO | WO 91/07876 | 6/1991 |
| WO | WO 91-07876 | 6/1991 |
| WO | WO 91/07876 A1 | 6/1991 |
| WO | WO 96/25916 | 8/1996 |

OTHER PUBLICATIONS

The American Heritage Dictionary, Second College Edition, 1982, p. 781.*
Chemical encyclopedia (ChE), vol. 5, M., "Great Russioan Encyclopedia", p. 283, article "Chloramine").
The Merck Manual, M., "Mir", 1997, vol. 2, p. 597.

* cited by examiner

*Primary Examiner*—Yong S Chong
(74) *Attorney, Agent, or Firm*—Fay Sharpe LLP; Karl W. Hauber

(57) ABSTRACT

The invention concerns the use of tosylchloramide(s), tosylchloramide salt(s), their derivatives and/or the decomposition products for treating diseases of the skin, mucous membranes, organs and tissues, excluding treatment of retroviral diseases (HIV) and disinfecting processes. It has been shown that tosylchloramide compounds can be used even for all diseases of the skin and viral mucosa causing formation of vesicles and itching, and they can lead to similar results as those obtained when they are used to treat corresponding diseases in tissues and organs. They not only provide quick relief of the acute symptoms and cure, but they also reduce frequency of recurrence. The inventive use is characterised in that it leads to very good treatment results, entirely independently of the form of preparation used, and it does not have to be administered in one specific manner. Relatively low amounts of tosylchloramide active principle can provide complete cure.

37 Claims, No Drawings

USE OF TOSYLCHLORAMIDE(S) FOR TREATING DISEASE OF THE SKIN, MUCOUS MEMBRANE, ORGANS AND TISSUES

The invention concerns the use of tosylchloramide(s) as effective substance for treating diseases of the skin, the mucous membranes, organs and tissues.

Today, as in the past, there are numerous diseases whose treatment is only possible to a sub-ordinated extent, since appropriate drugs for treatment do not yet exist. This is true, for example, with respect to viral diseases, such as herpes simplex, herpes labialis, herpes zoster, varicella as well as other vesicle-forming skin diseases. With the exception of local anesthesia, there are currently no effective medicines which will alleviate the itching.

In addition, several viral statica against herpes are known, which, however, primarily present strong side effect. Thus, until now, neurodermitis or psoriasis are only treatable with corticoid preparations. Furthermore, several diseases, such as acne and aphthae pose treatment problems and most of the substances obtainable in pharmacies produce more or less successful results with respect to healing and rarely afford relief.

According to the state of the art, several suggestions have been submitted relative to chloramine T, the tosylchloramide-sodium salt, which is specifically employed as disinfecting means. Disclosure of DE 39 13 391 A1 relates to a disinfecting- and medicinal means, containing a combination of chloramine T only in combination with a reduction means. Said means is employed specifically for fighting fish diseases in aquariums and commercially raised fish, for disinfection of fish hatcheries and swimming pool water, but also for disinfection of wounds in humans, mammals and birds. The object, on which said teaching is based, consists of elimination of toxic side effects of chloramine T, in particular in fish. For said purpose, a reduction means is added, such as, for example, sodium thiosulfate or similar.

According to the teaching of DE 41 37 544 C2, an antimicrobial combination of effective substances is described as an antiseptic and for disinfection of skin, mucous membranes and wounds, containing a multi-substance mixture of 0.025 to 3% of an oxygen-splitting and 0.01 to 3% chlorine-splitting compound, plus urea, allantoin, panthenol and/or lactic acid. The oxygen-splitting compound may be an inorganic or organic peroxide, hydroperoxide, a peroxy acid or its salt, whereas the chlorine-splitting compound constitutes sodium hypochlorite or tosylchloramide salt. The object of said technical teaching consists, in particular, in raising the low disinfecting effectiveness of the oxygen-splitting compounds, such as for example hydrogen peroxide, which is obtained by adding the above compounds.

The above described prior art is disadvantageous to the extent that combination preparations from different compounds must be employed, whereby the quantities and modes of effectiveness of the different components need to be adjusted to each other. Also, for all practically purposes, effective disinfection of the preparations ranks first, which is frequently combined with skin irritation. The state of the art discloses, according to WO 91/07876 A1, a remedy against retroviruses, in particular against the HIV-virus. Said means is applied onto objects, such as plastic equipment, medical instruments and similar in order to prevent transmission of infection. Moreover, utilization of a therapeutic compound against retro-viruses is also made available. Said means may contain chloramine T. The provided therapeutic compound prevents the activation of lymphocytic cells, where replication of the virus takes place, —in other words, there is no multiplication of HIV-viruses. Retro-viruses basically differ from the DNA-viruses which are to be treated according to the invention, such as, for example, the herpes viruses. Retro-viruses are encased viruses, having a diameter of 80 to 120 nm, whereby their genome comprises 2 RNA molecules, single stranded, and strand-positive oriented—with varied length between 8 to 11 kB. In addition, the genome of these viruses presents specific peculiarities, due to which there is a basic distinction between these viruses and other viruses.

Accordingly, the invention is based on the object of further developing the preparations of the initially described state of the art, so that additional treatment possibilities are made available for diseases, in particular skin- and mucous membrane diseases, which are practically free from side effect. Treatment method should be simple and be employed by means of as many application modes as possible. Moreover, treatment should have a broad spectrum of effectiveness and cover the largest possible range of diseases. There should be no restriction in the treatment with respect to a given application mode. Furthermore, the provided preparation should directly alleviate the occurring diseases and then cure them.

According to the invention, the above object is solved by the utilization of tosylchloramide(s), salts of tosylchloramide (s) and their derivatives and/or decomposition products for the treatment of diseases of the skin and mucous membranes, as well as organs and tissues, with the exception of treatment of retro-viral (HIV) diseases and disinfection.

Thus, it is possible to employ tosylchloramide, its salts, derivatives and decomposition products either individually or also in combination. The treatable diseases include, for example, viral diseases, such as herpes genitalis: the most widely spread venereal disease, herpes simplex, herpes labialis, chickenpox: zoster varicella-virus, shingles and herpes facialis: herpes zoster, itching of the skin, such as mosquito bites and also vesicle-forming skin, mucous membrane and tissue diseases, such as neurodermatitis, psoriasis, acne, aphtae, stomatitis aphthosa and stomatitis herpetica.

In a particularly preferred, specific embodiment of the invention, it is possible to treat skin and mucous membrane diseases, in particular such diseases which lead or may lead to "efflorescences". The term "efflorescences" stands for forms of morbid changes of the skin. These may be, for example, so-called primary efflorescences, which are directly caused by a disease. These are, for example: spots, nodules, superficial or more deeply located knots, tubera, tumors, swellings, skin eruptions, dilated, superficially extending blood vessels, pustulas, such as pus pustulas, blisters, cysts. So-called secondary efflorescences develop after the primary efflorescences and manifest themselves by scales, crusts, erosions, scrapings, cracks, tumors, scars, shrinkage and thickening of the skin.

By means of the inventive composition, such aspects of disease can, surprisingly, be directly alleviated and, as a rule, cured. Mitigation can, for example, consist in that the intensive itching disappears which is associated with diseases of the skin, mucous membranes, tissues or organs.

The diseases which are to be treated, presenting efflorescences or without efflorescences, may be caused by micro-organisms and/or accompanied by micro-organisms or may be due to parasitic effects. The term "micro-organism", within the framework of the invention, stands for both, bacteria, viruses (with the exception of retro-viruses), mycetes as well as zooparasites, which are likewise included here. This includes, for example, diseases like scabies, pediculosis or creeping eruption. With the inventively employed preparation, treatment can be specifically provided to the following:

a) the eye, in particular eye lid, cornea or conjunctiva of the eye; b) the ear, in particular the exterior of the ear; c) the nose, in particular the nasal cavity; d) lips and mucous membranes of the mouth, and/or the tongue; e) vulva and/or vagina; f) penis, in particular the glans penis and the prepuce; g) anus; h) nails, in particular the body and the wall and fold of the nail as well as root of the nail; i) hair, in particular hair follicles and sebaceous glands and j) hands and feet, in particular the spaces between fingers and toes.

According to a preferred specific embodiment of the invention, tosylchloramide salts are particularly employed as alkali and alkaline earth. Preferential employment of sodium- and calcium- as well as potash salt leads to outstanding results in treatment. Particularly preferred is sodium salt which is marketed under the trade name "chloramine T" by Synopharm of Barsbuettel (22882).

Depending upon the employed base, the active tosylchloramide ingredient is applied in the form of tosylchloramide, salt, derivative and/or decomposition product—singly or in combination—in an amount of approximately 0.1 to 20% by weight, preferably approximately 5 to 15% by weight, specifically approximately 8 to 12% by weight. "Base" within the framework of the present invention signifies the presentation form of the preparation, which is not particularly limited according to the invention. The preparation may be liquid, semi-solid, solid, be in the form of water-containing or water-free galenical preparations, such as ointments, gels, creams, pastes, suppositories, tablets, effervescent tablets, capsules, sticks, such as lipsticks, in pulverized form, powders, solutions, adhesive bandages, aerosols, two-compartment systems or suspensions, such as for example shaking mixtures/dry suspensions.

If the base is a gel, the active tosylchloramide ingredient is present in an amount of approximately 0.1 to 5% by weight, specifically approximately 0.1 to 2% by weight. With respect to gels, these may involve hydrocarbon gels. Hydrocarbon gels are water-free bases which distinguish themselves by appreciable chemical indifference and long keeping quality. Addition of preservatives is not required. Vaseline is preferably employed as base, its consistency can optionally be modified by solid or liquid paraffins, waxes and fatty alcohols. Hydrocarbon gels cover the treated areas of the skin in moisture-permeable fashion, resulting in the maceration of the stratum corneum. Consequently, the contained medicaments are generally able to penetrate into deeper layers of the skin. Therefore, application is indicated in the chronic stage of various dermatoses. Known bases for gels are also high-polymer polyethylenes and liquid paraffin, which differ in their melting behavior from Vaseline and which have a clearly higher dropping point.

Hydrogels are also suitable as base. Hydrogels are fat-free, washable bases, which are manufactured by gel formation of organic or inorganic auxiliary substances with high percentages of water (approximately 90 to 98%). Generally, they also contain moisturizing agents and preservatives. By way of organic gel developers, anionic compounds can be used, such as carboxy-methyl cellulose and alginate, or non-ionic macro-molecules such as methyl cellulose and hydroxy-ethyl cellulose. Such type of hydro-gels have initially a cooling effect and, after evaporation of the water, form a coating of dried-on film on the surface of the skin. In contrast thereto, with anionic poly-acrylates of the carbopol-type, hydro gels are obtained which can be rubbed into the skin and which therefore possess a certain depth effect. By neutralizing poly-acrylic acid with certain amines, alcohol-containing gels can be prepared with ethanol or isopropanol, which are capable of increasing the cooling as well as the depth effect. Hydrogels are preferably suited for treatment of neurodermatitis, psoriasis, acne, mosquito bites and apthae.

W/O emulsion ointments are preferably employed by way of ointments, such as adhesive- or eye ointments. Based on their lipophile outer phase, W/O emulsion ointments lubricate the skin and cannot be washed off with water. They contain one or several W/O emulsifiers, such as for example degras, degras alcohol, higher fatty alcohols or glycerin fatty acid ester. W/O emulsion ointments can be preserved; they frequently contain antioxidants. Their skin spreading property is excellent. In contrast to the O/W emulsions, the flow direction of the moisture of the skin is directed toward the interior of the skin under the influence of the lipophile outer phase of this type of ointment. This increases swelling and penetration. These basic characteristics are preferably suited for dry skin.

Another suitable ointment type are the O/W-emulsion ointments. O/W-emulsion ointments (creams) can be washed off, based on their watery outer phase. They generally contain complex emulsifiers whose hydrophilic component is formed by fatty alcohol sulfates or non-ionic polyethylene-glycol containing tensides. By way of lipophile stabilizers, use is made of fatty alcohols, sorbitan fatty acid ester or glycerin fatty acid ester. O/W-emulsions frequently contain moisturizing agents and, as a rule, need to be stabilized with preservatives. Because of their watery outer phase, creams can generally be easily distributed over the skin and have a cooling effect. O/W-emulsions are used in the treatment of sub-acute and sub-chronic dermatoses and are preferably suited primarily for the seborrheic type of skin. The O/W- or W/O-emulsion ointments are particularly appropriate in the treatment of herpes simplex, herpes labialis, herpes zoster, varicells and other vesicle-forming skin diseases. The active ingredient, tosylchloramide is contained in O/W- or W/O ointments in volume of preferably 0.1 to 20% by weight, particularly preferred approximately 5 to 15% by weight and most particularly preferred approximately 8 to 12% by weight.

A particularly preferred preparation contains 10% by weight of active tosylchloramide ingredient in a cortisone-containing adhesive ointment (0.001% by weight corticoid) such as Volon A, a brand name of Messrs. Squibb-Heyden GmbH. In said preparation, the active tosylchloramide ingredient is particularly effective, preferably with herpes simplex, herpes labialis, herpes zoster, varicells and other vesicle-forming diseases of the skin, including aphthae, stomatitis aphthosa and stomatitis herpetica.

Further possible bases are solid galenic preparations, such as pulverized substances, powders or pastes, which may be employed, for example, as bath water additives for hand-, foot- or full baths, and which contain the active tosylchloramide ingredient in an amount of approximately 0.1 to 20% by weight. When employed in form of powder, for use as an additive to bath water, it preferably contains a concentration of approximately 0.1 to 1% by weight (particularly with neurodermatitis). Solid preparations further comprise suppositories or vaginal beads—which dissolve and form a foam lining,—sticks for treating areas of the lips, skin or mucous membranes (in particular with herpes labialis), adhesive bandages, for example with tissue of natural or artificial origin, or both, either porous, or air- and moisture-tight, tablets, such as capsules of soft or hard gelatin, effervescent tablets and similar.

In addition, aerosols, such as sprays, can also be employed in gas-tight containers, which must be operated mechanically or are operated with FCKW-free propelling gas, such as spray mist, foam, gel or adhesive coating, which is generated on the areas of the skin or mucous membranes which are to be treated. Particular consideration is given in this regard to dosing aerosols or dosing solutions which release a defined volume of substance with each stroke or push. Two-component systems in gas-tight vessels may likewise be employed, in which the effective tosylchloramide substances are stored alone or with an inert carrier material and/or propellant in two separate chambers and are mixed only with each application.

The benefits related to the invention are multifold. It has been demonstrated that tosylchloramide compounds can be employed with all vesicle-forming, itching, viral-caused skin and mucous membrane diseases and lead to the same results—the same is true of corresponding diseases of tissues and organs. Not only is there attained rapid alleviation of the acute symptomatic, but as well a decline in the recidivism rate.

It is particularly surprising that the inventive employment of the active tosylchloramide ingredient leads to excellent treatment results, completely independent from the utilized base. One is not restricted to a given application mode. It is possible that already relatively low amounts of the active tosylchloramide ingredient will lead to full healing. In addition, as indicated above, the application form can be adapted to the specific requirements, so that ample variability is given with respect to presentation form.

The direct or local application, for example, in form of gels, salves, sticks or as a bath additive has the advantage that the affected location can be directly treated, that good adhesion is obtained, even with moist mucous membranes and—at the same time—it is possible to achieve long dwell and adsorption time. Of particular benefit is the galenic form of the spray, whereby with spraying on the painful or itching portions of the skin, application of the active ingredient can take place pain-free and without contact, in contrast to application of a salve, which is something which will surely increase patient's compliance. The local application initially leads to noticeable burning after a use and then to rapid mitigation of the acute complaints—healing of any efflorescenses occurs, as a rule, within just a few days. Treatment can already take place before development of possible efflorescenses, which are formed only in the last stage of a skin disease. It is precisely in the case of herpes that such efflorescenses are prevented through treatment, thus lending itself to preventive treatment as well.

Tosylchloramide compounds, such as chloramine T have long been known as disinfectants, which may also be employed for disinfection of drinking water and they are thus thoroughly tested with respect to their effectiveness, their elimination behavior, unwelcome effects, counter-indications, reciprocal interactions, toxicological properties, as well as mutative propensity, etc.

Therefore, the inventive applications seem to raise no inherent concern regarding compatibility upon direct contact with the skin and potential sensibilisation, such as for example the local application in appropriate concentration in combination with an ointment.

Additional properties and benefits of the present invention are apparent from the following exemplary embodiments, which are not intended to limit the invention-specific teaching. To the person skilled in the art, additional exemplary embodiments are obvious within the framework of the inventive disclosure.

EXAMPLES

The following examples 1-3 demonstrate, in detail, the preparation of some inventively applied bases. After that, treatment with the active tosylchloramide ingredient is described in Examples 4 to 7.

Example 1

Preparation of a W/O-Emulsion Ointment in Form of a Wool Wax Alcohol Salve

The wool wax alcohol salve was composed as follows:

| | |
|---|---|
| wool wax alcohols | 6.0 parts |
| cetyl stearyl alcohol | 0.5 parts |
| white Vaseline | 93.5 parts |

The substances were melted in a water bath and stirred until cooled. Up to 12 parts of Vaseline can be substituted by viscous paraffin. A preparation having the following composition was then prepared:

| | |
|---|---|
| Wool wax alcohol salve | 1 part |
| water | 1 part |
| tosylchloramide-sodium | 0.2 parts |

Into the wool wax alcohol salve, which had been heated to approximately 60° C., water was incorporated that had been heated to the same temperature. The salve was stirred until cooled and the tosylchloramide-sodium was then incorporated.

Example 2

Preparation of an O/W-Emulsion Salve in Form of a Hydrophilic Ointment

The hydrophilic ointment had the following composition:

| | |
|---|---|
| emulsifying cetyl-stearyl alcohol | 30 parts |
| viscous paraffin | 35 parts |
| white Vaseline | 35 parts |

The substances were melted in a water bath and stirred until cool. In the event that no easily spreadable ointment is obtained according to the cited prescription, viscous paraffin and white Vaseline may be exchanged with each other, as needed, by up to 10 percent. This salve was then used to prepare the following composition:

| | |
|---|---|
| hydrophilic salve | 30 parts |
| water | 70 parts |
| tosylchloramide-sodium | 14 parts |

The hydrophilic salve was melted in a water-bath at approximately 70° C. and mixed with small portions of water that had been heated to the same temperature. The salve was stirred until cool and the evaporated water replaced. Tosylchloramide-sodium was incorporated.

Example 3

Preparation of a Hydro-Gel Having the Following Composition

| | |
|---|---|
| hydroxy-ethylene cellulose 300 | 4.5 g |
| glycerol 85% | 30.5 g |
| purified water | 65.5 g |
| tosylchloramide-sodium | 2.0 g |

The hydroxy-ethylene cellulose was uniformly suspended, under stirring, in the freshly boiled and cooled-down water, in which the tosylchloramide has been dissolved. The mixture had to expand until clear gel had developed. After that, glycerol was stirred in. Evaporated water was replaced, if necessary.

Example 4

The hydrogel which had been obtained in Example 3 was applied onto mosquito bites. This resulted in rapid decline of itching. Blisters dried up within 24 to 36 hours, with healing of the skin after additional 24 to 36 hours.

Example 5

Chloramine T was mixed into the known adhesive ointment "Volon A", which contains corticosteroids and the following treatments were undertaken:

a) Aphtha:

An ointment, containing the inventively employed tosylchloramide substance, was applied on the aphthae. Following application, there occurred a brief burning sensation, after that one barely noted any sensitivity of the treated aphthae, whereupon rapid healing took place of the ulcus within a matter of 1 to 2 days. The apththae therapy also demonstrated that, contrary to the traditionally employed Zovirax ointment, application onto mucous membrane (mouth, region of genitalia) is possible and successful.

b) Herpes Labialis:

The broken-out herpes healed off in the shortest possible time, which made itself known by means of prickling or tingling. With timely recognition, as a rule, there will not be a break-out.

c) Rhagades in the Corner of the Mouth:

The course of the treatment corresponds to what was described under "herpes labialis". Here again, notice was taken of rapid and lasting healing. Generally, with herpes infection in the oral cavity, in particular at the hard palate, one obtains excellent treatment results with the inventively employed adhesive salve.

d) Neurodermatitis with Herpes Superinfection:

Instant decline in the unbearable itching was attained with concurrently amazingly rapid healing of the skin. For persons suffering from neurodermatitis, the elimination of itching is of utmost importance, since it does away with the irresistible urge to scratch, which frequently leads to further worsening and further spreading of the rash. Relief can be achieved with the inventively employed effective substance.

Example 6

Instead of adhesive salve Volon A with added chloramine T, a normal cooling salve was prepared—"unguentum leniens" which merely contained chloramine T-powder (2% by weight) as active ingredient, but no corticoid. The success described under Example 5 was the same. The utilization of a hydrolotion containing only chloramine T as active ingredient resulted in the above represented results. Even addition of the powder to the bath water brought comparable results.

Example 7

15 test patients with different aspects of disease were treated under control of a physician. After treatment over a period of several days, the physician made an evaluation with respect to effect and overall results of the treatment. For evaluation of effect, the following assessment grades could be assigned: "none"—"minor"—"good"—"very good"—"outstanding". For assessment of overall application results, it was possible to select from the following:

"no improvement"—"moderate improvement"—"good improvement"—"excellent improvement". The executed examinations with respective the various disease aspects and the obtained results are summarized in the Table which is shown below:

TABLE

| Test Patient | Disease Aspect | Base | Period of Application | Evaluation of Effect | Overall Result of Application |
|---|---|---|---|---|---|
| 1 | herpes labialis | Adh. ointment Volon A with Chloramine T | 5 days 2 times per day | very good | excellent improvement |
| 2 | herpes labialis | Adh. ointment Volon A with Chloramine T | 3 days 1-3 times per day | excellent | excellent improvement |
| 3 | herpes labialis | Adh. ointment Volon A with Chloramine T | 2 days 1-2 times per day | excellent | excellent improvement |
| 4 | herpes labialis | Adh. ointment Volon A with Chloramine T | 6 days 1-4 times per day | good | good improvement |
| 5 | herpes labialis | Adh. ointment Volon A with | 4 days 1-3 times per day | very good | good improvement |

TABLE-continued

| Test Patient | Disease Aspect | Base | Period of Application | Evaluation of Effect | Overall Result of Application |
|---|---|---|---|---|---|
| 6 | herpes labialis | Chloramine T Adh. ointment Volon A with Chloramine T | 2 days 1-2 times per day | excellent | excellent improvement |
| 7 | Aphthae | Adh. ointment Volon A with Chloramine T | 2 days 2-3 times per day | excellent | excellent improvement |
| 8. | Psoriasis | Ointment with 2% by wt. of chloramine T | 7 days 2-3 times per day | insignificant | moderate improvement |
| 9 | vesicles with watery liquid | ointment with 2% by wt. of chloramine T | 7 days 3-4 times per day | insignificant | moderate improvement |
| 10 | psoriasis of the scalp | ointment with 2% by wt. of chloramine T | 7 days 3 times per day | excellent | excellent improvement |
| 11 | lip rhagade | ointment with 2% by wt. of chloramine T | 4 days 1-3 times per day | excellent | excellent improvement |
| 12 | lip rhagade | ointment with 2% by wt. of chloramine T | 5 days 2 times per day | good | excellent improvement |
| 13 | stomatitis herpetica | ointment with 2% by wt. of chloramine T | 5 days 1-4 times per day | excellent | excellent improvement |
| 14 | neurodermatitis with herpes super-infection | ointment with 2% by wt. of chloramine T | 6 days 1-2 times per day | excellent | excellent improvement |
| 15 | Shingles | ointment with 3% by wt. of chloramine T | 20 days 1 time per day | excellent | excellent improvement |

The preceding results clearly demonstrate the surprisingly high effectiveness with utilization of the tosylchloramide compound according to the invention. Even psoriasis disappeared completely after a 7 day treatment. In just two cases of probably chronic disease aspect was it possible to achieve only moderate improvement.

The invention claimed is:

1. A method of topically treating efflorescence diseases of the skin and mucous membrane caused by herpes simplex virae, said method comprising the administration of a pharmaceutical preparation to the area to be treated for a patient in need thereof, wherein said preparation comprises alkali and/or alkaline earth salts of tosylchloramide.

2. The method of claim 1, wherein the diseases affect:
a) the lid, conjunctiva or cornea of the eye;
b) the exterior of the ear;
c) the nasal cavity;
d) the lips and mucous membranes of the mouth and/or the tongue;
e) the vulva and/or vagina;
f) the penis;
g) the anus;
h) the nail;
i) the hair follicles and/or the sebaceous glands; and/or
j) the hands and feet.

3. The method of claim 1, wherein said tosylchloramide salt(s), are present in an employed base in an amount of approximately 0.1 to 20% by weight.

4. The method of claim 1, wherein sodium tosylchloramide salt is employed.

5. The method of claim 3, wherein said base comprises a liquid, semi-solid or solid, water-containing or water-free galenic preparation.

6. The method of claim 5, wherein said base comprises an ointment, a gel, a cream, a paste, a suppository, an adhesive bandage, a tablet, a stick, a pulverized substance, a powder, a solution, an aerosol, a two-compartment system or a suspension.

7. The method of claim 5, wherein said base comprises a dosed aerosol or a dosed solution.

8. The method of claim 5, wherein said base comprises a bath water additive.

9. The method of claim 5, wherein said base is an O/W- or a W/O-emulsion ointment.

10. The method of claim 3, wherein said base is a cortisone-containing preparation.

11. The method of claim 5, wherein said base is a gel comprising said tosylchloramide salt(s), in an amount of approximately 0.1 to 5% by weight.

12. The method of claim 5, wherein a bath water additive is employed in form of pulverized substance or bath salt tablet or effervescent tablet, which is applied in water in a concentration of approximately 0.1 to 1% by weight.

13. The method of claim 1, wherein said tosylchloramide salt(s), are present in an employed base in an amount of approximately 5 to 15% by weight.

14. The method of claim 1, wherein said tosylchloramide salt(s), are present in an employed base in an amount of approximately 8 to 12% by weight.

15. The method of claim 5, wherein the base is a gel, in which are present said tosylchloramide salt(s), in an amount of approximately 0.1 to 2% by weight.

16. The method of claim 1, further comprising a treatment schedule including an application duration from about 2 to about 20 days and an application frequency from about 1 to about 4 times per day.

17. The method of claim 1, further comprising a treatment schedule including an application duration from about 2 to about 6 days and an application frequency from about 1 to about 3 times per day.

18. A method of topically treating efflorescence diseases of the skin and mucous membranes caused by the herpes simplex virae comprising:
   application of a pharmaceutically prepared medicament, to the area to be treated for a patient in need thereof, having a salt of tosylchloramide selected from the group consisting of alkali salts, alkaline earth salts and mixtures thereof in an employed base in an amount of approximately 0.1 to 20% by weight.

19. The method of claim 18, wherein said base comprises a liquid, semi-solid or solid, water-containing or water-free galenic preparation.

20. The method of claim 19, wherein said base comprises an ointment, a gel, a cream, a paste, a suppository, an adhesive bandage, a tablet, a stick, a pulverized substance, a powder, a solution, an aerosol, a two-compartment system or a suspension.

21. The method of claim 19, wherein said base comprises a dosed aerosol or a dosed solution.

22. The method of claim 19, wherein said base comprises a bath water additive.

23. The method of claim 19, wherein said base is an O/W- or a W/O-emulsion ointment.

24. The method of claim 18, wherein said base is a cortisone-containing preparation, containing said tosylchloramide salt(s), in an amount of approximately 0.1 to 20% by weight.

25. The method of claim 19, wherein said base is a gel comprising said tosylchloramide salt(s), in an amount of approximately 0.1 to 5% by weight.

26. The method of claim 19, wherein the bath water additive is employed in form of pulverized substance or bath salt tablet or effervescent tablet, which is applied in water in a concentration of approximately 0.1 to 1% by weight.

27. The method of claim 18, wherein said tosylchloramide salt(s), are present in an employed base in an amount of approximately 5 to 15% by weight.

28. The method of claim 18, wherein said tosylchloramide salt(s), are present in an employed base in an amount of approximately 8 to 12% by weight.

29. The method of claim 19, wherein the base is a gel, in which are present said tosylchloramide salt(s), in an amount of approximately 0.1 to 2% by weight.

30. A method of topically treating efflorescence diseases of the skin and mucous membrane caused by herpes simplex virae, said method comprising:
   applying a pharmaceutical preparation to the area to be treated, for a patient in need thereof, including alkali and/or alkaline earth salts of tosylchloramide, wherein said tosylchloramide salts are present in an employed base in an amount of approximately 0.1 to 20% by weight;
   said applying of said preparation comprises a treatment schedule; and,
   wherein said schedule comprises an application duration from about 2 to about 20 days and an application frequency from about 1 to about 4 times per day.

31. The method of claim 30, wherein the base comprises a liquid, semi-solid or solid, water-containing or water-free galenic preparation.

32. The method of claim 6, wherein said suppository is a vaginal suppository.

33. The method of claim 6, wherein said tablet is selected from the group consisting of an effervescent tablet, a vaginal tablet, and a capsule.

34. The method of claim 6, wherein said suspension is a shake mixture/dry suspension.

35. The method of claim 20, wherein said suppository is a vaginal suppository.

36. The method of claim 20, wherein said tablet is selected from the group consisting of an effervescent tablet, a vaginal tablet, and a capsule.

37. The method of claim 20, wherein said suspension is a shake mixture/dry suspension.

* * * * *